United States Patent [19]
Björling et al.

[11] 4,454,094
[45] Jun. 12, 1984

[54] TEST INDICATOR FOR SUBSTANCES IN LIQUIDS

[75] Inventors: Karl T. Björling, Tumba, Sweden; Ann-Marie M. S. Grönberg, London, England

[73] Assignee: Alfa-Laval AB, Tumba, Sweden

[21] Appl. No.: 438,861

[22] PCT Filed: Mar. 1, 1982

[86] PCT No.: PCT/SE82/00057
§ 371 Date: Oct. 14, 1982
§ 102(e) Date: Oct. 14, 1982

[87] PCT Pub. No.: WO82/03127
PCT Pub. Date: Sep. 16, 1982

[30] Foreign Application Priority Data
Mar. 2, 1981 [SE] Sweden .................................. 8101322

[51] Int. Cl.³ ............................................. G01N 21/78
[52] U.S. Cl. ......................................... 422/56; 422/57; 435/14; 435/27; 435/805
[58] Field of Search ....................... 422/55, 56, 57, 58; 435/805, 14, 27

[56] References Cited
U.S. PATENT DOCUMENTS 3,723,064  3/1973  Liotta .
3,798,004  3/1974  Zerachia et al. ...................... 422/56
3,964,871  6/1976  Becton .
4,046,513  9/1977  Johnson .......................... 23/253 TP
4,181,501  1/1980  Keese et al. ...................... 422/57 X

FOREIGN PATENT DOCUMENTS 2416047  10/1975  Fed. Rep. of Germany ........ 422/56
2729333   2/1978  Fed. Rep. of Germany .
2922856   2/1980  Fed. Rep. of Germany .
2934760   3/1980  Fed. Rep. of Germany .
2029138  10/1970  France .

Primary Examiner—Arnold Turk

[57] ABSTRACT

An indicator is disclosed, which is intended for detecting at least one test substance in a test medium, comprising a carrier and a reaction system consisting of at least a first reactant and a second reactant, applied separately on the carrier, said first reactant being intended to travel by diffusion to the second reactant through a parth in the carrier, soaked by the test medium, while reacting with the test substance.

The indicator is characterized in that the first reactant is applied within at least one limited locality, while the second reactant is applied within at least one locality, on a varying distance from the locality of the first reactant.

7 Claims, 11 Drawing Figures

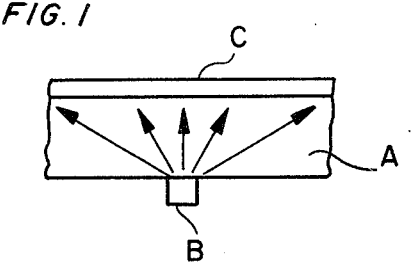
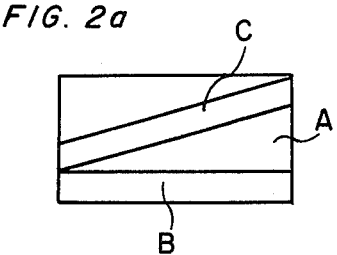
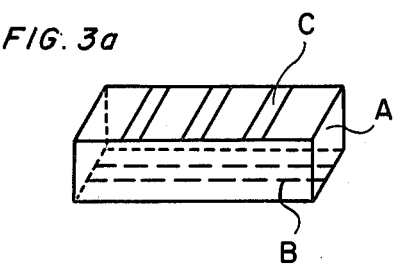
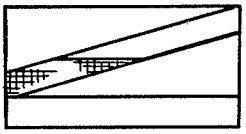
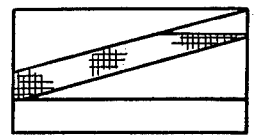
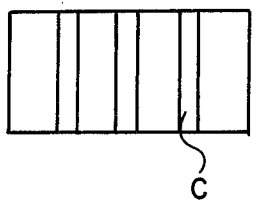
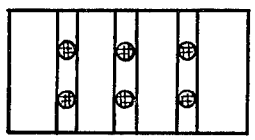
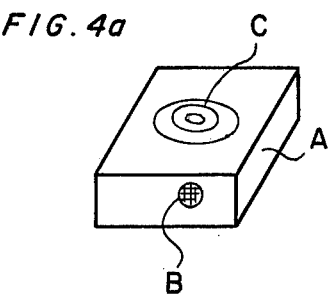
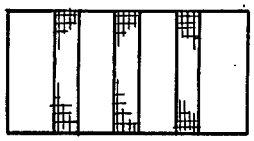
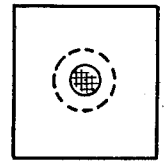
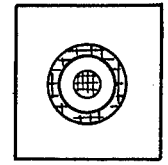

TEST INDICATOR FOR SUBSTANCES IN LIQUIDS

The present invention relates to an indicator for detecting at least one test substance in a test medium, comprising a carrier and a reaction system, consisting of at least a first reactant and a second reactant, applied separately on the carrier, said first reactant being intended to travel by diffusion to the second reactant through a path in the carrier, soaked by the test medium, while reacting with the test substance.

An indicator of this type is disclosed in U.S. patent application Ser. No. 806,687 now abandoned, in which there is disclosed e.g. an indicator for detecting of the enzyme catalase in milk. The reaction system employed consists partly of a first enzyme for generating hydrogen peroxide, namely glucose and the enzyme glucose oxidase, and partly of a color-generating system consisting of the enzyme peroxidase and o-tolidine, which latter is converted from a colorless state into a colored state, if it is allowed to react with hydrogen peroxide. In principle, the first, hydrogen peroxide-generating system is applied to a carrier in a distance to the color-generating system. When the test shall be performed, the carrier—preferably a paper strip—is soaked with the test medium, that is to say the milk. Hydrogen peroxide is evolved, which travels by diffusion in the direction towards the color-generating system. On its way the hydrogen peroxide has to travel by diffusion through a part of the carrier, which is soaked by test medium. If this contains the substance sought, catalase, the latter will react with the hydrogen peroxide to an extent, that is determined by its concentration, and no or a limited quantity of the hydrogen peroxide generated can travel by diffusion to the color-generating system to give rise to a color. The intensity of the color thus depends on the concentration of any remaining hydrogen peroxide and thus inversely on the concentration of catalase in the test medium.

This indicator may give good results, but these are dependent on a number of factors. The accuracy of the catalase determination thus demands an exact time schedule for the measuring procedure, good light and a color scale for comparison between the color developed and the color scale, provided with catalase concentration figures at different color tinges. The color tinge may show considerable variation depending on variations in the color of the milk itself, disturbing substances in the milk or the air, and the age of the indicator. The color tinges in the color system peroxidase-o-tolidine may also vary with different charges in commercial production.

The objective of the present invention is to provide an indicator which has none of the mentioned drawbacks. Such an indicator is characterized, according to the invention, in that the first reactant is applied within at least one limited locality, while the second reactant is applied within at least one locality in a varying distance from the locality of the first reactant.

By this design of the indicator the first reactant, e.g. hydrogen peroxide, will travel by diffusion along paths of different length through the carrier towards the second reactant, e.g. a color generating system like peroxidase-o-tolidine, and thereby be consumed to a greater or smaller extent, according to the provision of test substance of the type sought in the part of the carrier, which is situated between said localities, and which is soaked by the test medium. A longer path of diffusion gives on opportunity for a higher degree of reaction between the first reactant and the test substance which means that a correspondingly less amount of the first reactant can reach the second reactant to form e.g. a color. It is probably most convenient to use such reaction systems, which give rise directly to a visually detectable color change, even if other reaction systems could be considered, e.g. such systems, in which the color is only developed by spraying a developer on it.

Suitably the indicator is made of a plane material, like a paper sheet or the like as a carrier.

In one embodiment of the indicator according to the invention the first reactant is applied as a first band on a surface of the carrier, and the second reactant is applied as a second band in such a way, that the distance from the first band to the second band varies, suitably continuously.

It may also be convenient to design the indicator in such a way that the first reactant is applied on one side of the carrier and the second reactant is applied on the other side. Thereby an especially good effect is obtained, if the first reactant is applied within one locality in the form of a band, oriented into a first direction, and the second reactant is applied within several localities in the form of bands, substantially mutually parallel, into a direction which differs from said first direction, and is preferably perpendicular to said first direction.

In a further embodiment of the invention the first reactant is applied onto one side of a carrier, within a locality which has a substantially circular limit, and the second reactant is applied to the other side of the carrier within localities in the form of a number of concentric rings provided with mutual distances. In use a distinct number of rings is colored/not colored.

The invention is not, per se, limited to any special mode of manufacture, but is probably quite suitable to apply the reactants by printing technique, known per se.

The invention shall now be described more in detail, reference being made to the enclosed figures, of which:

FIG. 1 shows an indicator in the form of a paper strip, in longitudinal section, grossly enlarged.

FIG. 2 shows an indicator, provided with reactant on one side surface, seen from above.

FIG. 3 shows an indicator provided with reactants on both sides, partly perspectively, to some degree sectionally, and partly in use, seen from above, and FIG. 4 shows, in a similar way, another embodiment of an indicator with reactants on both sides.

The indicator shown in FIG. 1 consists of a paper strip on the lower side of which there has been applied a first reactant B, in the form of a transversal band and the upper side of which is coated with reactant C. When used, the complete strip is soaked in the sample, which is to be investigated, the carrier thus being impregnated with test substance A. When reactant B is simultaneously brought into contact with the test medium, usually a liquid, a mobile reactant, liberated from B, starts to travel by diffusion in the direction of the arrows shown. Thereby a certain amount of the liberated reactant will travel by diffusion straight to the upper side, whilst other amounts will have longer and longer ways of diffusion to reactant C. At a certain concentration of test substance A in the test medium, the chances for the liberated reactant to reach reactant C will decrease, the longer diffusion way there is, as the probability for it to react with test substance A increases with increasing diffusion path. This will mean, that a relatively great concentration of liberated reactant will reach reactant C closest to reactant B, and a relatively low concentration will reach reactant C further away. If C is a reactant, which will show a color directly when reacted with liberated reactant, this will mean a correspondingly decreasing color tinge with increased diffusion path.

The indicator in FIG. 2 is provided with a band of reactant B and a band of reactant C, the bands forming an acute angle. In FIG. 2a the indicator is shown before usage, in FIG. 2b, when used for the analysis of a test medium with a relatively high concentration of test substance A and FIG. 2c, when used for the analysis with relatively low concentration of A.

The indicator, shown in FIG. 3 is provided, on the lower side, with reactant B applied as longitudinal bands and on the upper side with transversal bands of reactant C. FIG. 3b shows the indicator when used for the analysis of a sample with a high concentration of A, FIG. 3c for the analysis of a sample with a moderately high concentration of A, and FIG. 3d for the analysis of a sample with a low concentration of A.

FIG. 4 shows, in a corresponding way, an indicator, provided on the lower side with reactant B in the form of a small round spot, and on the upper side provided with a number of concentric rings of reactant C, separated from each other. FIG. 4a shows the indicator when used for the analysis of a sample with a relatively high concentration of A and FIG. 4c shows the indicator for the analysis of a sample with a relatively low concentration of A.

The indicator according to the invention has the following advantages, as compared to indicators, which have been used previously for similar purposes:

1. The sensitivity of the indicator for a test substance can be varied within wide limits, by using carriers with adapted resistance to diffusion, e.g. in the form of paper sheets of suitable thickness.

2. The color scale can be printed in black/white as it is rather the color pattern than the color tinge that determines the measuring result.

3. The reading of the indicator is simple and can be performed by non-skilled staff.

4. The reading result is relatively insensitive to factors like light, color of sample, disturbing components in the sample, etc.

5. The time schedule for reading of the indicator is less critical, in practical cases within an interval of some minutes.

6. The indicator can be manufactured, advantageously, by conventional printing technique.

The indicator can be used for concentration measurement of a number of substances, especially enzymes. In the examples shown, the first reactant is e.g. glucose, applied separated from, but in the vicinity of glucose oxidase, and the other reactant is peroxidase mixed with o-tolidine. Such an indicator can be used for the measurement of the concentration of catalase in milk.

The indicator can also be used, advantageously, for the determination of other substances than enzymes. Thus an indicator for the determination of total acid concentration (expressed e.g. as mM $H^+$) can be designed according to the example just disclosed, with a reactant B consisting of an alkaline substance, like sodium hydroxide, and a reactant C consisting of a pH-indicator with a suitable detection interval, e.g. bromthymol blue for neutral pH. When soaking the indicator with test liquid, the alkaline substance will travel by diffusion through the test liquid reacting with any acid available, and any remaining alkaline will be indicated by the reactant C.

We claim:

1. A device for indicating the presence of a defined substance in a liquid test medium comprising a substantially inert permeable substrate of substantially uniform thickness, a first reagent deposited in a first area of said substrate and being capable, upon contact with said test medium, of releasing a mobile substance capable of reacting with said defined substance, and a second reagent deposited in a second area of said substrate remote from said first area, and said second reagent being capable of changing color upon contact with said mobile substance, certain portions of said second area being more remote from the nearest portion of said first area than are other portions of said second area.

2. The device claimed in claim 1 wherein one of said first and second areas is smaller than the other.

3. The device claimed in claim 1 wherein one of said areas comprises a series of concentric circular bands and the other is located at the center of said concentric bands.

4. The device claimed in claim 3 wherein one of said areas is located on one side of said substrate and the other area is located on an opposite side of said substrate.

5. The device claimed in claim 1 wherein the areas are bands on the surface of the substrate.

6. The device claimed in claim 5 wherein said bands diverge.

7. The device claimed in claim 5 wherein the bands are on opposite sides of the substrate and are perpendicularly positioned with respect to one another.

* * * * *